United States Patent [19]

Rittenburg et al.

[11] Patent Number: 5,942,444
[45] Date of Patent: Aug. 24, 1999

[54] MARKING OF PRODUCTS TO ESTABLISH IDENTITY, SOURCE AND FATE

[75] Inventors: James H. Rittenburg, Perkasie, Pa.; Robin Jenkins, Appleton Roebuck, United Kingdom

[73] Assignee: Biocode, Inc., Cambridge, Mass.

[21] Appl. No.: 08/788,392

[22] Filed: Jan. 27, 1997

[51] Int. Cl.$^6$ .................................................. G01N 33/543
[52] U.S. Cl. .............................. 436/518; 435/4; 435/7.1; 435/9; 436/2; 436/8; 436/29; 436/543
[58] Field of Search ........................... 106/31.01; 208/12; 252/182.13; 427/444; 435/4, 7.1, 9; 436/518, 543, 2, 8, 20, 22, 23, 24, 29

[56] References Cited

U.S. PATENT DOCUMENTS

| | | | |
|---|---|---|---|
| 4,764,290 | 8/1988 | Currey | 252/11 |
| 5,006,362 | 4/1991 | Hilborn | 427/3 |
| 5,110,833 | 5/1992 | Mosbach | 521/50 |
| 5,310,648 | 5/1994 | Arnold et al. | 435/5 |
| 5,429,952 | 7/1995 | Garner et al. | 436/518 |
| 5,525,516 | 6/1996 | Krutak et al. | 436/56 |
| 5,541,342 | 7/1996 | Korhonen et al. | 548/532 |
| 5,587,273 | 12/1996 | Yan et al. | 430/269 |

FOREIGN PATENT DOCUMENTS

| | | |
|---|---|---|
| 95/21673 | 8/1955 | WIPO . |
| 87/06383 | 10/1987 | WIPO . |
| 93/05068 | 3/1993 | WIPO . |
| 93/09075 | 5/1993 | WIPO . |
| 94/14835 | 7/1994 | WIPO . |

OTHER PUBLICATIONS

Mosbach et al., The Emerging Technique of Molecular Imprinting and Its Future Impact on Biotechnology, Bio/Technology, 14(2):163–170 Feb. 1996.

Wulff, G., "Molecular Imprinting . . . — A Way towards Artificial Antibodies," Angewandte Chemie, 34(16):1812–1832 Sep. 1995.

*Primary Examiner*—Carol A. Spiegel
*Attorney, Agent, or Firm*—Clark & Elbing LLP

[57] ABSTRACT

In general, the invention features a method of marking a product for identification in which a marker, composed of a print molecule, print molecule analogue, or molecularly imprinted molecule, are added to the product and subsequently measured in a specific binding assay.

10 Claims, No Drawings

MARKING OF PRODUCTS TO ESTABLISH IDENTITY, SOURCE AND FATE

BACKGROUND OF THE INVENTION

This invention relates to the marking of products to establish their identity, source, and fate.

Major problems experienced in many areas of the world and in connection with many different products is that of product counterfeiting, unauthorized distribution and sale of a product (e.g. grey market trading, parallel trading, product diversion), as well as false liability based on product substitution.

Throughout the world, manufacturers provide the products they sell with a visually distinctive appearance, packaging or labels so that customers can distinguish their products from those of others. As a result, their customers learn to associate the visually distinctive appearance with certain standards of quality, and, if they are satisfied with those standards, will buy products provided with that visually distinctive appearance in preference to others. Once customers have acquired a preference for products provided with a particular visually distinctive appearance, the manufacturers become vulnerable to product counterfeiting.

A counterfeit product consists of a product that is provided with a visually distinctive appearance, or a brand name, confusingly similar to that of a genuine product. Customers seeing the visually distinctive appearance or the familiar brand name provided to the counterfeit product, buy this product in the expectation that they are buying a genuine product.

There are many ways known of providing products with a visually distinctive appearance. In general, the visually distinctive appearance is provided either directly to the product or to an article with which the material is associated, for example a label, wrapper or container. The visually distinctive appearance may be, for example, a distinctive shape or configuration, a distinctive marking, or a combination of the two. A particularly preferred visually distinctive appearance is a trademark.

The material of a counterfeit product may be the same as, or different from the material of a genuine product. Often the material of the counterfeit product is the same, but of inferior quality. For instance, it is usually difficult to distinguish a chemical product having a particular chemical formula and made by one manufacturer, from the same chemical, with the same formula, but made by a different manufacturer. This is particularly so if the two manufacturers use the same production process. For this reason, it is not difficult for the unscrupulous to establish the chemical formula of an active ingredient in a composition, and the relative amounts of the various ingredients in the composition, and then pass off his own product as that of another manufacturer.

In addition to product counterfeiting, product adulteration is another major problem. Product adulteration takes place when a product is tampered with such as by dilution. An example of such a problem lies in the adulteration of lubricating oils, or other oil-based products, by addition of a counterfeiter's oil to a genuine product. Such adulteration is not only financially damaging to the oil manufacturer but the consequent lowering of performance which can occur can cause damage to the consumer and consequently harm the reputation of the genuine product. A method of overcoming this problem has been previously proposed involving the incorporation of a visible dye in the product. Such a strategy is easily copied.

The following patent documents are hereby incorporated by reference.

WO 87/06383 discloses a method of labelling an item or substrate by means of macromolecules, in particular, DNA or proteins. European patents 0327163 and 0409842, and U.S. Pat. No. 5,429,952 disclose methods of marking products with chemicals that can be measured by immunoassay or by other specific binding assays.

U.S. Pat. Nos. 5,304,493, 5,244,808 and 4,918,020 disclose methods of marking petroleum products with dyes and subsequent detection of the dyes using standard solid phase extraction technology.

WO 95/21673, WO 94/14835, WO 93/09075, WO 93/05068, and U.S. Pat. Nos. 5,310,648 and 5,110,833 all disclose methods for preparing imprinted polymers that subsequently maintain the ability to selectively bind the imprinting chemical.

SUMMARY OF THE INVENTION

In general, the invention features a method of marking a product for identification. The marker is a chemical entity consisting of either a print molecule, a structurally related analogue of a print molecule, or a molecularly imprinted molecule (MIP) which specifically binds to the print molecule (referred to herein as an "anti-print MIP"). The marker is non-deleterious to the product and not already associated with the product. Thus, the presence of the marker can only be easily established by someone who knows the identity of the marker, but cannot be routinely determined by a counterfeiter or other person unfamiliar with the marker. Thus, a counterfeit and a genuine product can be distinguished by the absence of the marker in the former and the presence of the marker in the latter.

The product is generally a commercial product and may be either solid, liquid, semisolid liquid, semisolid or gas. The marker may be added directly to the product (e.g., attached to a surface of the product or mixed with the product itself) or associated with a label, tag or other product packaging material.

The invention also features kits for detecting a marker(s) in a marked product. One version of a detection kit includes a sample-receiving solid support which has the print molecule bound to its surface, a container containing an anti-print MIP, and detecting means for detecting print--anti-print MIP complexes. Preferably, the detecting means is a detectably labeled print molecule or analogue which specifically binds the MIP. Preferred detectable labels include enzymes, chemiluminescors (e.g. luciferin), and chromophores (e.g. dyes, colored latex beads, dyed particles, pigments, metal sol particles (e.g. gold or silver metal sol particles), dye encapsulated liposomes, carbon). Another version of the detection kit includes a sample receiving solid support comprising an anti-print MIP and a container containing a detectably labeled print molecule. A third version of the detection kit includes a sample receiving solid support comprising a first anti-print MIP and a container containing a detectably labeled second MIP.

One class of markers of the invention are chemical compounds having a detectable physical characteristic, (e.g. color). The physical characteristic of the marker is not detectable at marker concentrations present in the marked product, but is detectable upon concentration of the marker. The print marker is thus detected by concentrating it from a sample of the marked product to provide the marker at a concentration which allows detection of the concentration-dependent, physical characteristic of the marker. In preferred embodiments, the marker is concentrated from the sample by use of a molecularly imprinted solid phase extraction (MISPE) column that specifically binds the marker.

The invention also features a kit for detecting markers having a detectable, concentration-dependent, physical characteristic. The kit includes a sample receiving solid support which contains a MISPE sorbent.

In preferred embodiments, the molecularly imprinted molecule comprises a homo- or hetero-polymer of functional monomers selected from the group consisting of acrylic acid, methacrylic acid, ethylene dimethacrylate, vinyl pyridine, sulfonic acid, vinylimidazole, and itaconic acid.

In other preferred embodiments, the print molecule is an amino acid, peptide, or a protein. In other preferred embodiments, the print molecule is a nucleic acid or a nucleotide base; a sugar composed of galactose, glucose, fucose, fructose, or mannose; or a metal ion selected from the group consisting of $Cu^{2+}$, $Cd^{2+}$, $Fe^{3+}$, $Co^{2+}$, $Zn^{2+}$, $Ni^{2+}$, and $Mg^{2+}$.

By "molecularly imprinted molecule" or "anti-print MIP" is meant any macromolecule that has been prepared by cross-linking subunits in the presence of the print molecule such that the resulting molecule retains an imprint of the print molecule and will subsequently specifically bind the print molecule.

By "marking a product for identification" is meant associating a marker with a product so that the source, identity, or other information about the product including production date, batch, and shelf-life may be established. Identification of a marked product can also facilitate: 1) monitoring of manufacturing or other processes, including monitoring process streams and blending controls; 2) product monitoring for security or regulatory purposes, such as marking the source country of products for customs and marking regulated substances; 3) detecting and monitoring spillages of marked materials, including the detection of residues of marked products, such as pesticides, herbicides, fertilizers, toxic wastes, organic pollutants (such as TBT and dioxins) and other chemicals; 4) tracing a product, such as marking a process chemical to monitor the rate of addition of the chemical to a system (e.g. a water system) in order to optimize chemical dosage; and 5) studies of biodegradation of a compound, e.g. in soil biodegradation studies. Marking a product for identification also includes associating a product with a particular concentration of a marker, so to facilitate the detection of product adulteration by way of dilution, concentration changes, or the addition of foreign substances.

By "physical characteristic of a marker" is meant a characteristic inherently associated with a marker, such as color, fluorescence, luminescence, density, weight, and optical activity.

By "concentration-dependent physical characteristic" is meant a physical characteristic which is only detectable at a particular concentration of a compound. As used herein, "concentration-dependent physical characteristic" particularly refers to a physical characteristic of a marker which is not detectable at the marker concentration employed in a marked product, but which is detectable upon concentration of the marker (e.g. by extraction and concentration of the marker from the marked product, to a concentration greater than the marker concentration in the marked product).

The present invention allows the practitioner to, for the purposes of marking a product, employ a print molecule which will be specifically recognized at low concentrations by an anti-print MIP and which provides characteristics useful for a particular product marking application. Such marker characteristics may include: (1) solubility or non-solubility in a product or solvent; such solubility or non-solubility can be important either for efficiently incorporating the marker into the product, or for extracting the marker for testing; (2) stability during extremes of temperature, pH or other physical or chemical conditions inherent in many manufacturing processes, (3) stability within a product or adherence to the surface of a product during conditions of use or storage.

Furthermore, as described in WO 95/06249, the marker can also be chemically attached to other molecules to create "tagged" compounds that can be used for the purpose of marking. In the context of the present invention, the tag portion of these "tagged" compounds would be recognized by a specific binding member.

Print/anti-print binding assays, analogous to immunoassay, are employed to test a product for a marker in a remote location by relatively inexperienced personnel. Specific binding pair assays and related techniques, such as MISPE concentration coupled to physiochemicals methods of analysis (e.g. HPLC and fluorometry), allow for the use of accurate reference procedures in the laboratory. This combined ability to test in both the field and the laboratory allows products to be screened for a marker on location and/or sent to a secure laboratory for testing, depending on which mode of testing is most appropriate for the application.

Other features and advantages of the invention will be apparent from the following description of the preferred embodiments thereof, and from the claims.

DETAILED DESCRIPTION

Markers (Print Molecules or Anti-Print MTP'S)

The marker of the invention is capable of being detected by a specific binding pair assay and/or by concentration of the marker using the anti-print MIP (when the marker is a print molecule) or a print molecule (when the marker is an anti-print MIP) and detection of a concentration-dependent physical characteristic. The marker should be compatible, i.e., non-deleterious, with the product which it marks. The marker may be a print molecule or an anti-print MIP. One important point is that the print molecule which is used to make the anti-print MIP need not be exactly the same as the print molecule used as a marker or, when the marker is an anti-print MIP, the specific binding molecule used to detect the anti-print MIP. The situation is analogous, in this respect, to antibody-antigen tests, where an antigen used to generate the antibody need not be identical to the antigen used to detect the antibody in the test. Preferably the marker will be non-toxic if used in a manner in which it is intended to be ingested. Preferably the marker is visually undetectable when present in the product.

The marker should in general be one which is not normally present in the chemical or composition; for example, it is not a by-product of the production process, normal impurity, or standard additive for that chemical, or chemical composition. In preferred embodiments, the marker compound is present in very low concentrations, e.g., in the order of parts per million or parts per billion. Although the marker is preferably inert with respect to the product in the sense that it does not react with the product which it labels, it must nevertheless be capable of binding to a specific binding member, (e.g. a molecularly imprinted molecule). Moreover, the ability to detect the marker should not be adversely affected by interaction with the product or compound it labels. For example, where the marker is to be detected by a specific binding assay, the marker is still capable of binding to its complimentary binding partner.

Depending on the specific application, certain criteria must be considered in selecting an appropriate chemical compound which is capable of performing acceptably as a marker. Most importantly, the compound must possess a specific molecular moiety, which is recognizable to a specific binding member (e.g., a specific MIP). Exemplary marker compounds may typically include substituted aromatic compounds such as atrazine, cholesterol, and diaminoanthraquinone.

A wide range of compounds are suitable as marker compounds so long as they are compatible with and non-deleterious to the product being marked. Thus oil-compatible, water-compatible and solids-compatible or food grade compounds can be used as marker compounds, dependent on the product being marked.

The use of optically active marker compounds may be particularly advantageous, as it is difficult to distinguish between optically active forms of compounds by conventional analytical techniques, particularly when only trace quantities of the compound are available for analysis. Molecularly imprinted molecules which are selective for a particular optically active form of a compound can be produced to facilitate detection of such optically active marker compounds in a product.

In a preferred embodiment of the invention, the marker has a detectable physical characteristic. Detectable physical characteristics of a marker include, for example, color, weight, density, magnetic attraction, luminescence, fluorescence, absorbance, chemical reactivity, or various characteristics which can be detected by optical methods well known in the art. Preferably the physical characteristic of the marker is color or fluorescence. Preferably, detection of the physical characteristic of the marker is not possible at the low concentrations of marker present in a marked product. Upon concentration of the marker from a product sample (e.g. by MISPE concentration) to a concentration that is greater than the marker concentration in the marked product, the physical characteristic is readily detectable by, for example, detection of a particular color of the concentrated test sample. Preferably, the marker may be detected by its physical characteristic following at least a 2-fold increase, preferably at least about a 5-fold increase, more preferably at least about a 10 to 10,000 fold increase in marker concentration relative to the concentration of the marker in the marked product. Exemplary markers which may be detected by a concentration-dependent physical characteristic include Safranin O and Rhodanile blue.

The marker compound may be associated with the product in a wide variety of ways. Thus the marker compound may be present in or on all or part of the product, or in or on all or part of a label, wrapper or container associated with the product. The marker compound is usually mixed with the product, but may alternatively be incorporated in the substance of the product packaging material or printed on the surface of the product or product packaging.

Products for marking

The product marked may be solid, semi-solid, fluid, or gas.

Examples of solid products include polymers, plastics, and rubbers; pharmaceutical tablets, capsules and powders; solid formulations of agrochemicals such as insecticides, herbicides, fungicides and fertilizers; textiles such as clothing; designer or specialty products such as crystal, china, and silver goods; original works of art such as paintings and sculptures, recordings such as gramophone records, tape cassettes, floppy discs and compact discs; electrical goods such as television sets, computers and radios; motor vehicle components and cameras; paper such as documents, confidential papers, notes, securities, labels, and packaging; chemical products such as biocides, cosmetics such as creams; and food products.

Examples of fluid products include oil-based products such as lubricating oils, gasoline, diesel and liquified petroleum products; paints and coatings; perfumes; cosmetics; inks; drinks such as wine, whiskey, sherry, gin and vodka; liquid pharmaceutical formulations such as syrups, emulsions and suspensions; liquid agrochemical formulations; chemical compositions; and industrial solvents. The fluid product is preferably liquid. One preferred class of products encompasses oil based products such as lubricating oils.

Examples of gases include stack emissions (e.g. for pollution tracing), air parcels (e.g. for study of weather patterns), air samples within storage containers (e.g. to ensure that such containers have not been opened) and chlorofluorocarbons (e.g. difluorodichloromethane, tetrafluoromethane, octafluorocyclobutane, trichlorofluoromethane, etc.) used in aerosol propellents, air conditioning and refrigeration.

When the product is a liquid, the marker compound is preferably colorless at concentrations present in the marked product and soluble in the liquid product so that its presence can only be detected by subsequent assay. It is preferably also odorless at marker concentrations present in the marked product.

Preferably only trace quantities of marker are used. Typically a marker compound will be incorporated with a product at a concentration in the range of from 1 part per billion (ppb) to 25 parts per million (ppm). Preferably the concentration will be in the range of from 20 ppb–500 ppb. Where the marker is to be assayed through direct detection of the marker on the surface of the product (e.g. in an ink or coating placed on the product surface), the percent incorporation of the marker into the polymer will generally be in the range of about 0.1% to 5% by weight. In some cases the molecularly imprinted molecule may be printed or placed on the product surface and subsequently detected with a complimentary binding member having a detectable label.

The ability to detect concentrations of marker compound at very low concentrations, i.e., in the parts per billion range, is a particular advantage of the method according to the invention. Thus only small quantities of marker compound need to be used.

Another particular advantage of the invention is that binding pairs based on molecular imprinting often bind best in organic solvent matrices which are less polar than water. This is particularly useful in detecting markers directly in fuels and other petroleum products without the prior need of extracting the marker into an an aqueous environment. Other types of specific binding assays, such as immunoassay, generally require that the sample to be analyzed is predominantly aqueous.

Preferably several markers are included in chemical or chemical composition products. The ratios of the concentrations of the markers in each chemical or composition labelled are then preferably unit ratios, e.g. in the case where there are two markers the ratio of concentration of one to that of the other may be 1:1, 1:2, 1:3, 1:4, etc. The total amount of marker compound(s) added is such that each marker compound is preferably added at a level of not more than 10 parts per million, and more preferably at not more than 100 parts per billion (by weight).

In one embodiment, a plurality of markers are present that possess a common site which enables them to bind to, and be concentrated on, the same specific binding member, while they remain separable by subsequent analytical techniques. Thus in some embodiments the print molecule may be comprised of an amino acid or short (2–30 amino acids) peptide; or a nucleotide or short (2–30 nucleotides) oligonucleotide. The print molecule analogues used as markers will maintain the basic structural component of the print molecule but will also contain additional amino acids or nucleotide structure which can be varied to provide for multiple marking combinations. The markers can subsequently be extracted from the marked product using MISPE specific to the print molecule. The purified and concentrated markers may then be further analyzed by size, charge, or polarity separation on an SDS-PAGE gel or by HPLC.

In one application of the invention, a marker is applied to a surface using an impact or non-impact printing method. The laid down marker can be subsequently visualized by the application of the other member of the specific binding pair. In one embodiment of the invention the marker will be comprised of a molecularly imprinted molecule, such as a molecularly imprinted version of a polyacrylate binder typically used in inks.

Alternatively, the marker can be incorporated into coatings which are then applied to the surface of a product to be marked. Exemplary coatings include paints, varnishes, plastic or rubber-based coatings, as well as other coatings well known in the art. These coatings can be applied to credit cards, pressure sensitive labels, security labels, holograms, product packaging, or other visual mark of authenticity (e.g. a trademark or logo). The marker-labeled coatings can be applied directly to the surface of products (e.g. electronic equipment, appliances, photographs, glass, metal, and plastic). Detection of the marker in the coating may be performed by assaying a sample of the product coating. Alternatively, the marker in the coating may be detected by directly assaying the surface of the marked product in a reversible, non-destructive manner through reaction with a detectably labeled specific binding member specific for the marker in the coating. Once the marker is visualized on the surface of the product, the specific binding member may be dissociated from the marker by various methods well known in the art including changes in ionic strength, polarity, or pH. Preferably, the dissociation will be performed by a method which preserves the marker intact to allow for future visualizations.

In one embodiment of the method, the MIP is dissolved or suspended in an ink formulation capable of being applied through ink jet printing or other printing methods known in the art. Once dry, the MIP can be revealed by application of the specific binding pair linked to a signal compound such as an enzyme, latex bead or fluorescent tag.

Marker detection

The markers may be detected in a sample of the product either qualitatively or quantitatively. Quantitation of the marker in a product facilitates detection of product adulteration by dilution of the original product.

Quantitation of the marker can also be used in assessing the physical parameters of fluid systems. For example, one can mark a known volume of a liquid (e.g. water) at a known concentration, add this marked sample to a fluid system of unknown volume, disperse the marked sample in the fluid system, assay a sample from the fluid system, and calculate the dilution effect to determine the volume of the fluid system.

The marker compound can be incorporated with the product in an aqueous or non-aqueous medium, and an assay to detect the marker may be carried out directly on a sample thereof. The sample may be filtered to remove solids, if necessary.

In general, producing a sample of a product to assay for a marker will comprise one or more steps selected from extraction of the marker compound from the product; dilution of the product with an aqueous or an organic solvent; filtration; evaporation; precipitation; and solid phase extraction of the marker compound, e.g. purification of the marker compound using an ion exchange resin, chromatography (e.g. using silica), or MISPE chromatography.

The solvent chosen for extracting the marker compound from the product prior to assay naturally depends on the natures of the product and the marker. Depending upon the natures of the product and the marker, the solvent will in general comprise one or more of water; hydrocarbons, for example benzene, toluene, xylene, hexane, heptane and octane; sulphoxides, for example dimethylsulphoxide; halogenated hydrocarbons; chlorinated solvents, for example chlorobenzene, methylene chloride, chloroform and carbon tetrachloride; ethers, for example diethyl ether, dioxane and tetrahydrofuran; amides, for example dimethylformamide and dimethylacetamide; nitrites, for example acetonitrile; alcohols, for example methanol, ethanol and propanol; esters, for example ethyl acetate; and ketones, for example acetone. Optionally the extraction solvent may also comprise buffer salts such as Tris buffer (Tris[hydroxymethyl] amino-methane). The solvent system used preferably yields the extracted marker compound in a liquid phase suitable directly for the subsequent detection assay. Obviously, in some cases where the marked sample is a liquid, no sample preparation or extraction will be required.

The present invention facilitates the identification of several different batches of a product (e.g. a chemical or chemical composition) by the use of a single marker compound. This is because a single marker compound may be employed in different concentrations in different batches and each batch identified by determination of the concentration of the marker in that batch.

In certain preferred embodiments a plurality of markers are included in a chemical or composition. In this case the number of possible permutations of concentration and markers is increased and batches may be identified with increased certainty by measuring relative concentrations of the markers.

In some embodiments of the present invention the marker is extracted from the product into a solvent before detection. Where the detection method uses a specific binding member (e.g. a MIP), the solvent is preferably one which is compatible with the specific binding member. Alternatively, where the extraction solvent is incompatible with the specific binding member the extract may be diluted with a compatible solvent before binding to the specific binding member.

Specific binding members are molecules which substantially specifically bind to the marker to be detected in a sample of a marked product. Exemplary specific binding member-marker pairs include MIP-print molecule, MIP-print molecule analogue, print molecule-MIP, and print molecule analogue-MIP. The specific binding member or members are desirably bound on a solid support, such as an MISPE column.

In a preferred embodiment, assay of the marker by contact with a complimentary binding member is accomplished by competitive enzyme-linked specific binding assay, although other assay methods may be employed, including enzyme-mediated binding assay, sandwich binding assays, binding assays using lateral flow devices, and other specific binding assays well known in the art.

Numerous variations on each of these assay methods are well known in the art. For example, the sandwich assay may be performed in at least three different manners. First, the sample receiving support may have a surface-bound MIP which specifically binds a marker (print molecule) to capture the marker on the support. Binding of the print molecule marker is then detected by the binding of a second, detectably-labeled MIP which specifically binds to another portion of the print molecule marker.

Alternatively, the marker (print molecule) may be bound to the support through non-specific (ionic, hydrophobic, etc.) or covalent interactions between the marker and the support surface or a coating on the support surface. For example, the marker may be bound to the support through an ionic interaction between the marker and the support (e.g. binding of BSA to polystyrene in a microtiter plate well). Methods for increasing such non-specific interactions are well known in the art (e.g. coating the support surface with a charged molecule to increase ionic interaction with the marker). Also the marker can be attached through covalent interactions such as through the use of carbodiimide to covalently couple carboxlic acid moeties to primary amine moieties. In this example, a detectably labeled (e.g., enzyme) MIP can be mixed with sample containing marker (print molecule) and solid phase marker (print molecule). The amount of detectably labeled MIP remaining bound to the solid phase marker provides an indication of marker concentration in the sample.

In another variation of the binding assay, the support-bound MIP can be brought into contact with a mixture containing the sample to be analyzed for marker (print molecule) and a fixed amount of detectably labeled marker (print molecule). The amount of detectably labeled marker remaining bound to the solid phase MIP provides and indication of the amount of marker in the sample. Actual detection of the result of the assay may be by colorimetric means or by alternative detection means such as chemiluminescence or fluorescence.

In a further embodiment of the invention, the marker has a detectable, concentration-dependent physical characteristic, such as color or fluorescence. While the marker is preferably not detectable in the product, the physical characteristic of the marker becomes readily detectable upon concentration of the marker to a concentration greater than the marker concentration in the product (i.e., detection of the physical characteristic is concentration-dependent). Thus, detection of such marker is accomplished by concentrating the marker from the product by, for example, precipitation, immunoprecipitation or other methods known in the art. Generally, the marker may be detected by its physical characteristic following at least a 2-fold increase, preferably at least about a 5-fold increase, more preferably at least about a 10 to 10,000 fold increase in marker concentration relative to the concentration of the marker in the marked product. Where the detectable, concentration-dependent physical characteristic is color, the presence of the marker may be detected by direct observation or by use of a spectrophotometer.

Preferably, the marker is concentrated by contacting a sample of a product with a specific binding member, preferably a MIP. The MIP may be packed into a column or presented in solution. The product sample is contacted with the MIP for a time sufficient for formation of specific complexes of marker (print molecule) and MIP. Where the MIP is in solution, the complexes are concentrated (e.g. precipitated). Upon binding of the marker to the support-bound MIP, or upon concentration of the MIP-marker complexes, the physical characteristic of the marker becomes readily apparent.

Such detection methods are well suited to field operation, as no complex laboratory equipment is required.

Production of MTP's for product marking applications

Molecular imprinting is a process whereby a chemical to be imprinted (print molecule) is mixed with other polymerizable entities (e.g., monomers) which are subsequently cross-linked to form a polymer or macromolecule. During the polymerization process, the print molecule forms bonds with the polymerizable entities in the reaction mixture. The print molecule (e.g., marker) is then extracted from the formed polymer or macromolecule leaving behind a three dimensional imprint, or recognition site, in the polymer or macromolecule, where the spatial arrangement of the polymer network corresponds to the imprinted molecule.

A wide range of substances can be imprinted, with many examples having been detailed in the literature. Several recent reviews have been published summarizing various applications of molecularly imprinted molecules (Mosbach and Ramstrom, Biotechnology Vol.14 February 1996; Muldoon and Stanker, Chemistry and Industry, Mar. 18, 1996; Wulff, Angew. Chem. Int. Ed. Engl. 34, 1812–1832). Substances to which MIP's have been made include: carbohydrates, amino acids, peptides, proteins, therapeutic drugs, steroids, metal ions, aromatic hydrocarbons, dyes, phosphonate esters, nucleotides, co-enzymes, pesticides, and hormones. The areas of application that have been prepared for Mip's include: 1) use as a chromatographic media with specific separation characteristics, 2) antibody and receptor binding site mimics in recogintion assay systems, 3) enzyme mimics for catalytic applications, and 4) recognition elements in biosensors and other assay systems.

In product marking applications the MIP can serve as a complementary binding partner, imparting specificity to the separation and analysis of a marker from a marked sample. In many ways MIP's are functionally analagous to antibodies in that they possess bindings sites that specifically interact with other chemical substances through a combination of ionic interactions, hydrogen bonding, P1–Pi-interactions, and hydrophobic interactions. Several of the advantages that MIP's have over antibodies in regards to product marking include the reduced time and cost of generating the binding molecule, and the ability to specifically bind marker in organic solvent matrices. In addition the MIP's are highly stable to harsh matrix conditions such as high temperature, pressure, pH, and organic solvents which generally will cause an antibody to degrade or deform in such a way that its binding ability is lost. The added stability of the MIP increases its potential use as both a binding element in a diagnostic test and as a marker that can be incorporated into or onto a product. A potential limitation in producing a MIP is that relatively large quantities of the print molecule is required. This can be a problem for certain applications (e.g. clinical diagnostics) where the analyte can be very costly or difficult to obtain. However, it is not an issue for product marking applications, since the chemicals generally selected as markers are inexpensive and commercially available in large quantity. The following table summarizes many of the desirable characteristics of MIP's:

TABLE 1

Characteristics of Molecularly Imprinted Polymers

| Feature | Characteristics | Reference |
| --- | --- | --- |
| Physical Stability | Resistant against mechanical stress, high pressures, and elevated temperatures | Anderson et al., In Molecular Interactions in Bioseparations, T. T. Ngo, (Ed.) Plenum Press New York, 383–395, 1993 |
| Chemical Stability | Resistant against acids, bases, various organic solvents, and metal ions | Kriz et al., Anal. Chem. 67:2142–2144, 1995 |
| Storage Endurance | >8 months without loss of performance | Fischer et al., J. Am. Chem. Soc., 113: 9358–9360, 1991 |
| Capacity | 0.1–1.0 mg print molecule per g polymer | Kempe et al., Tetrahedron Lett. 36: 3563–3566, 1995 |
| Imprint Memory | Repeated use > 100 times without reduction | Fischer et al., J. Am. Chem. Soc., 113: 9358–9360, 1991 |
| Recovery Yield | >99% | Anderson et al., J. Chromatorgr., 516: 167–79, 1990 Muller et al., Makromol. Chem. Rapid Commun, 14: 637–641, 1993 |
| Binding Strength | mM range (determined by chromatography nM range (determined by radioligand assay) | Kempe et al., Anal. Lett., 24: 1137–1145, 1991 Anderson et al., Proc. Natl. Acad. Sci. USA 92: 4788–4792, 1995 |

Marker detection kits

According to a further aspect of this invention we provide an assay kit for detecting the presence of a visually undetectable marker associated with a product, comprising means for providing a sample of said marker in a liquid medium, assay means including MIP's specific for the marker compound, detection means for monitoring the assay and means for comparing the result of the immunoassay with the result expected from a genuine product.

A means for providing a sample of said marker in liquid medium may comprise any solvent necessary for bringing the marker into solution and/or filtration means to remove unwanted solids and/or solid phase extraction columns (for example columns containing an ion exchange resin or a chromatography medium such as silica).

An assay means will employ marker specific MIP's and may also include a solid or semi-solid support having sample-receiving areas. Exemplary sample-receiving supports include test tubes, microtiter plates, dipsticks, membranes, lateral flow devices, resins, PVC or latex beads, and nitrocellulose filters. The sample receiving areas of the support have surface-bound capture reagent capable of binding to a specific binding member (e.g., a marker specific MIP) or surface bound MIP specific for a marker. Surface-bound marker may be conjugated to a protein or other polymeric compound which is capable of presenting an epitope of the marker for binding by a specific MIP.

A detection means for monitoring the result of the immunoassay may be, for example, means to produce and/or measure a detectable reaction. Thus a detection means may comprise an enzyme and a substrate for the enzyme. Preferred detectable labels include enzymes (e.g. horseradish peroxidase, alkaline phosphatase), chemiluminescors (e.g. luciferin), and chromophores (e.g. dyes, colored latex beads, dyed particles, pigments, metal sol particles (e.g. gold or silver metal sol particles), dye encapsulated liposomes, carbon). The detectable label may be attached to the marker, the MIP, or a second antibody directed against the marker. It will be appreciated by those skilled in the art that various configurations of "hybrid assays" can be conceived which utilize MIP'S in combination with other specific binding members such as antibodies. Examples of substrates for the detection of the label include tetramethylbenzidine (TMB), ABTS, o-phenylenediamine dihydrochloride; Amerlite Signal Reagent (available from Amersham International PLC); p-nitrophenol phosphate; and luciferase. It will be appreciated that an external detection device such as a spectrophotometer, luminometer or fluorimeter may be employed. In this way not only the existence of the marker compound but also the amount present can be determined, thus giving an indication of the extent of adulteration of the product.

Another embodiment of the invention features a kit for qualitatively or quantitatively detecting a marker by virtue of a concentration-dependent, physical characteristic of the marker. The kit includes a means for concentrating the marker from a sample of a product. The concentrating means may be provided as a solid support having surface-bound MIP specific for the marker. Binding of marker from the sample or sample extract serves to concentrate the marker, thus facilitating detection of the physical characteristic (e.g. color) of the marker. The solid support may be, for example, a molecularly imprinted solid phase extraction column, microtiter plate well, a test tube.

The kits described above may also include a means for comparing the result of the detection assay with that expected from a genuine product, and may comprise instructions describing the result expected of a genuine product (comprising, for example, a colour chart, calibration table or calibration curve), or it may comprise a sample of marked material identical to marked genuine product (to be analyzed alongside the unknown sample).

The kit is preferably provided with a representation of the visually distinctive appearance provided to the material of the genuine product. For example the kit may be provided with a representation of a trademark with which the material of the genuine product is provided.

The ability to provide assay means in kit form ensures that a person in the field, such as a distributor of a product in an environment distant from the product source can quickly check the authenticity of the product without recourse to laboratory facilities.

Because the marker compound is in such low concentrations in the labelled chemical or composition, its presence therein is not immediately apparent to someone who is unaware of the addition. Furthermore, it would not be easy for a third party to identify the marker using routine techniques and include it in a counterfeit composition. That is because isolation and concentration of the marker relies on the use of a specific binding member specific for the marker and this would not be available to anyone who was ignorant of the identity of the marker.

The invention will now be further described with reference to the following examples.

EXAMPLE 1

Preparation of MIPS for Atrazine

Atrazine specific MIP's can be prepared in the following manner. Atrazine (Chem Services, West Chester, Pa.) (the print molecule)(1.128 g) is added to 250 ml of chloroform (EM Science, Gibbstown, N.J.) in a 250 ml Erlenmeyer flask. To this solution is added 1.8 g of methacrylic acid (Aldrich Chemical, Milwaukee, Wis.) (MAA) and 18.7 g of ethylene glycol dimethacrylate (Aldrich Chemical, Milwaukee, Wis.)(EGDMA). This is followed by 0.24 g of 2,2 azobis (isobutryonitrile) (Chem Services, West Chester, Pa.). The reaction mixture is then capped with a vented rubber septum and sparged with helium for 5 minutes while in a sonicating water bath at 60° C. After about 30 minutes, a white, glossy polymer will begin to form in the flask. The reaction is allowed to proceeed for a total of 23 hours after which time the solvent will have completely evaporated. The flask is then placed in a vacuum oven at 60° C. for a minimum of 15 hours. The polymer is then removed and ground by hand using a mortar and pestle. The ground polymer is then sieved with water through a 25 $\mu$m sieve and recovered by filtration on No. 1 Whatman filter paper. The powder (<25 $\mu$m) is then sedimented in acetonitrile (5×50 ml) to remove the fine material. The coarse polymer is then extracted with chloroform (5×30 ml) to remove residual print molecule, and vacuum oven dried at 60° C. The MIP is then ready for use, or can be stored at room temperature.

EXAMPLE 2

MIP based assay of marked fuel

Atrazine (1 mg) is dissolved in methanol (10 ml) to give a 100 $\mu$g/ml stock solution. One ml of the atrazine stock solution is then added to a 1 liter volumetric flask and brought to a final volume of 1 liter with commercial, unleaded gasoline. This provides a gasoline sample containing 100 ng/ml or 100 ppb of atrazine as trace marker.

A molecularly imprinted sorbent extraction (MISPE) column is prepared by packing 100 mg of the MIP powder from Example 1 into a solid phase extraction cartridge (Lida Manufacturing Corp., Kenosha, Wis.). To analyze fuel for the presence of atrazine marker, 10 ml of the marked gasoline is passed through the MISPE column. The column will selectively remove the atrazine from the gasoline concentrating it on the MISPE column. Residual fuel is purged from the column using air and then the atrazine is eluted from the column using 2 ml of distilled water. The aqueous eluent containing the purified and concentrated atrazine is then assayed either in the field using immunoassay (atrazine Rapid™ Assay, Strategic Diagnostics, Newark Del.) or in the laboratory using standard HPLC methodology (Ramsteiner, J. Chromatography 1989 465 410–416).

In one experiment, conducted by Mark Muldoon in the laboratory of Dr. Larry Stanker at USDA, College Station, Tex., gasoline was marked with one ppm atrazine and 10 ml of the marked fuel was passed through a column containing a packing of 250 mg of the above-described atrazine MIP. Prior to application to the column, the column was washed successively with 25 mL $CHCl_3$, 25 mL 10% Hac/AcN, 10 mL AcN, and 10 mL $CHCl_3$.

After application of the marked gasoline to the column, column was rinsed with 10 mL $CHCl_3$. Atrazine was eluted with 10 mL 10% Hac/AcN. The 10% Hac/AcN fraction was evaporated to dryness and reconstituted into mL of AcN (5× concentrate).

The unpurified gasoline residue was made to volume 2 mL in AcN and diluted an additional 1:2 (to give a final 1:10 dilution). 25 $\mu$L of the solution were injected into an HPLC column (RPC-18, microbore, 225 nm monitored). For ELISA analysis, 200 $\mu$L of the 5× concentrate was evaporated to dryness and reconstituted in one mL PBS (1× concentrate). This solution was diluted an additional 1:200 PBS prior to ELISA analysis. A control sample of unmarked gasoline was tested in parallel. A second control tested atrazine marked gasoline applied to a control column containing polymer which was not atrazine-imprinted.

The recoveries of atrazine, as measured by ELISA, were as follows: control No. 1 (no atrazine in the gasoline sample): 0.0%. Control No. 2 (1 ppm atrazine in the gasoline sample, non-imprinted polymer in column: 25.4%. Test sample (1 ppm atrazine in the gasoline sample, atrazine-imprinted polymer in column): 98.3%.

Other embodiments are within the following claims:

What is claimed is:

1. A method of marking a liquid, organic, non-aqueous product for identification and then detecting said marked product, said method comprising
    a) associating a marker with the product, said marker being inert and non-deleterious with respect to the product and not already associated with the product, said marker being either (i) a print molecule or (ii) a molecularly imprinted, polymeric anti-print molecule which specifically binds to said print molecule, wherein the polymeric anti-print molecule is a synthetic, non-naturally-occurring polymer,
    b) forming a specific binding complex between said marker and either (i) said molecularly imprinted, polymeric anti-print molecule or (ii) said print molecule, respectively; and
    c) detecting said marked product by detecting said specific binding complex, wherein said detecting is carried out directly in a sample of said product without prior extraction into an aqueous phase.

2. The method of claim 1 wherein said molecularly imprinted, polymeric anti-print molecule comprises a homo- or hetero-polymer of functional monomers selected from the group consisting of acrylic acid, methacrylic acid, ethylene dimethacrylate, vinyl pyridine, sulfonic acid, vinylimidazole, and itaconic acid.

3. The method of claim 1 wherein said print molecule is a compound containing a metal ion selected from the group consisting of $Cu^{2+}$, $Cd^{2+}$, $Fe^{2+}$, $Co^{2+}$, $Zn^{2+}$, $Ni^{2+}$, and $Mg^{2+}$.

4. The method of claim 1 wherein said marker is a print molecule selected from the group consisting of dyes, fluorophores, and chemiluminescors.

5. The method of claim 1 wherein said marker is a print molecule which has a physical characteristic which is detectable in a concentration-dependent manner and said specific binding complex is detected by concentrating said print molecule and detecting said physical characteristic.

6. The method of claim 1 wherein said associating step comprises adding said marker to said product.

7. The method of claim 6 in which said adding step comprises mixing said marker with said product.

8. The method of claim 7 in which said product is a petroleum product.

9. A method of monitoring or tracing a liquid organic, non-aqueous process chemical or specialty additive, said method comprising:
    (a) associating said chemical or said additive with a marker, said marker being inert and non-deleterious with respect to said chemical or additive and not already associated with said chemical or additive, said marker being either (i) a print molecule or (ii) a molecularly imprinted, polymeric anti-print molecule which specifically binds to said print molecule, wherein said polymeric anti-print molecule is a synthetic non-naturally occurring polymer;
    (b) obtaining a sample from the process or product in which said chemical or additive is employed;
    (c) forming a specific binding complex between said marker in said sample and said (i) molecularly imprinted, polymeric anti-print molecule or (ii) said print molecule, respectively; and (d) measuring the concentration of said specific binding complex in said sample without extracting said sample into an aqueous phase to monitor or trace said chemical or additive.

10. The method of claim 9 wherein said chemical or additive is selected from the group consisting of a biocide, a water treatment chemical, a food additive, a plastics additive and a petroleum product additive.

* * * * *

UNITED STATES PATENT AND TRADEMARK OFFICE
CERTIFICATE OF CORRECTION

PATENT NO. : 5,942,444
DATED : August 24, 1999
INVENTORS : James H. Rittenburg and Robin Jenkins It is certified that error appears in the above-identified patent and that said Letters Patent is hereby corrected as shown below:

In Col. 4, line 35, replace "MTP'S" with --MIP's--;

In Col. 8, line 23, replace "nitrites," with --nitriles--;

In Col. 9, line 36, replace "and" with --an--;

In Col. 10, line 7, replace "MTP'S" with --MIP's--;

In Col. 10, line 34, replace "Mip's" with --MIP's--;

In Col. 10, line 46, replace "P1-Pi" with --pi pi--; and

In Col. 13, line 4, replace "2.2" with --2,2--.

Signed and Sealed this

Tenth Day of April, 2001

Attest:

NICHOLAS P. GODICI

Attesting Officer  Acting Director of the United States Patent and Trademark Office